United States Patent
Schader et al.

(10) Patent No.: US 10,675,411 B2
(45) Date of Patent: Jun. 9, 2020

(54) DRUG DELIVERY DEVICE WITH CARTRIDGE PIERCING WHEN CAP IS PULLED OFF

(71) Applicant: SANOFI-AVENTIS DEUTSCHLAND GMBH, Frankfurt am Main (DE)

(72) Inventors: Marc Schader, Frankfurt am Main (DE); Michael Helmer, Frankfurt am Main (DE); Sebastian Braun, Darmstadt (DE); Markus Ploch, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 144 days.

(21) Appl. No.: 15/736,617

(22) PCT Filed: Jun. 15, 2016

(86) PCT No.: PCT/EP2016/063698
§ 371 (c)(1),
(2) Date: Dec. 14, 2017

(87) PCT Pub. No.: WO2016/207040
PCT Pub. Date: Dec. 29, 2016

(65) Prior Publication Data
US 2018/0256820 A1    Sep. 13, 2018

(30) Foreign Application Priority Data
Jun. 22, 2015  (EP) .................................... 15173167

(51) Int. Cl.
*A61M 5/24* (2006.01)
*A61M 5/32* (2006.01)
*A61M 5/20* (2006.01)

(52) U.S. Cl.
CPC ........ *A61M 5/2466* (2013.01); *A61M 5/3202* (2013.01); *A61M 5/2033* (2013.01); *A61M 2005/247* (2013.01)

(58) Field of Classification Search
CPC .............. A61M 5/2466; A61M 5/3202; A61M 2005/247; A61M 5/2033
See application file for complete search history.

(56) References Cited

U.S. PATENT DOCUMENTS 3,368,557 A    2/1968  Vagn et al.
4,378,015 A *  3/1983  Wardlaw ............. A61M 5/2033
                                                    604/137
(Continued)

FOREIGN PATENT DOCUMENTS

EP          3108915      12/2016
WO       WO 97/14455     4/1997
(Continued)

OTHER PUBLICATIONS

International Search Report and Written Opinion in International Application No. PCT/EP2016/063698, dated Sep. 30, 2016, 11 pages.
(Continued)

*Primary Examiner* — Bradley J Osinski
(74) *Attorney, Agent, or Firm* — Fish & Richardson P.C.

(57) ABSTRACT

The disclosure relates to a drug delivery device for dispensing a liquid drug through a needle with a proximal and a distal needle tip, comprising
  a body,
  a needle holder holding the needle relative to the body,
  a cartridge holder holding a cartridge comprising the liquid drug sealed with a septum on a distal end and with a movable stopper on a proximal end, and
  a cap adapted to cover at least the distal needle tip of the needle, (Continued)

wherein the cartridge holder is movable relative to the body from a retracted position towards an advanced position, thereby piercing the proximal needle tipthrough the septum, characterized in that the cap is releasably engaged with the cartridge holder, wherein the cap is released from the cartridge holder in its advanced position.

11 Claims, 4 Drawing Sheets

(56) References Cited

U.S. PATENT DOCUMENTS

| | | |
|---|---|---|
| 2012/0041384 A1 | 2/2012 | Finke et al. |
| 2012/0179109 A1 | 7/2012 | Takemoto et al. |
| 2015/0073352 A1 | 3/2015 | Finke et al. |

FOREIGN PATENT DOCUMENTS

| | | |
|---|---|---|
| WO | WO 2007/100899 | 9/2007 |
| WO | WO 2010/072644 | 7/2010 |
| WO | WO 2015/055592 | 4/2015 |

OTHER PUBLICATIONS

International Preliminary Report on Patentability in International Application No. PCT/EP2016/063698, dated Dec. 26, 2017, 8 pages.

* cited by examiner

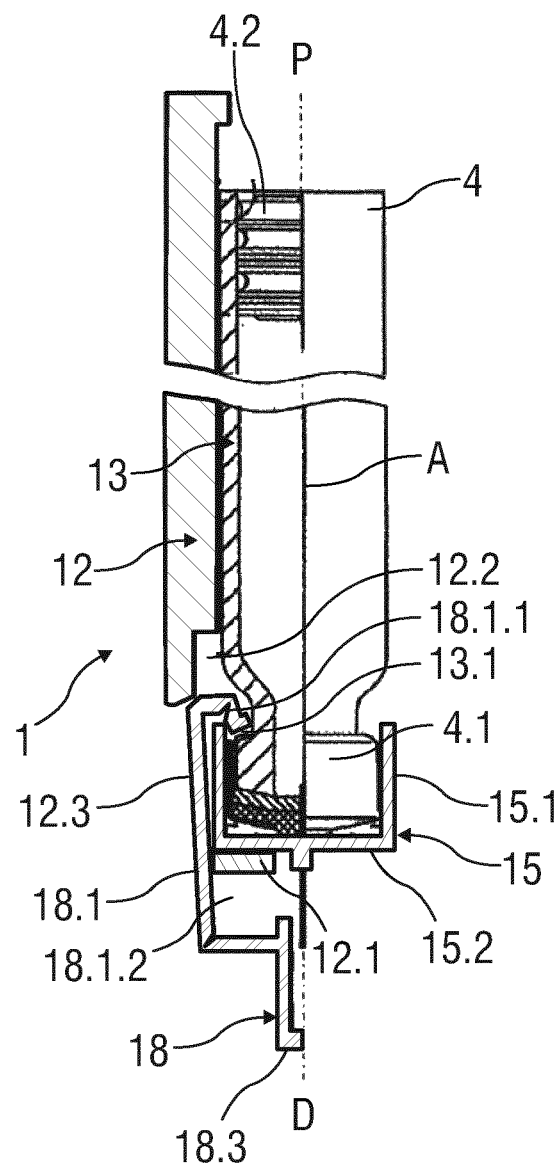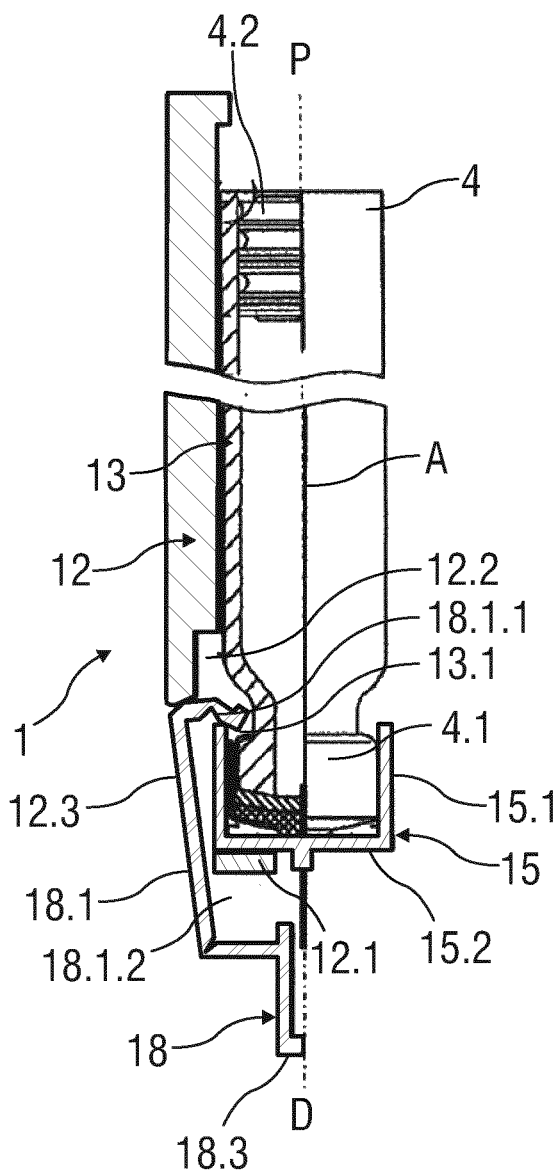

_DRUG DELIVERY DEVICE WITH CARTRIDGE PIERCING WHEN CAP IS PULLED OFF_

CROSS REFERENCE TO RELATED APPLICATIONS

The present application is the national stage entry of International Patent Application No. PCT/EP2016/063698, filed on Jun. 15, 2016, and claims priority to Application No. EP 15173167.6, filed in on Jun. 22, 2015, the disclosures of which are expressly incorporated herein in entirety by reference thereto.

TECHNICAL FIELD

The disclosure relates to a drug delivery device for delivering a liquid drug stored in a cartridge that is sealed with a septum, wherein the drug delivery device comprises an injection needle that is covered by a cap.

BACKGROUND

Pre-filled cartridges with a liquid drug are well known in connection with drug delivery devices to deliver the liquid drug by means of an injection needle with a distal needle tip adapted to penetrate tissue. To prevent a negative impact on the liquid drug during storage, yet to ease the preparation of an injection, it is known from the state of the art to seal pre-filled cartridges with a septum that is penetrated by a proximal needle tip of the injection needle immediately before the injection. Also, caps for covering at least the distal needle tip of an injection needle in order to prevent accidental needle sticks are known for such drug delivery devices. According to the state of the art, a user removes the cap and loads a pre-filled cartridge into the drug delivery device such that the proximal needle tip of the injection needle pierces through the septum of the pre-filled cartridge in order to prepare an injection.

SUMMARY

Certain aspects of the present disclosure can be implemented to provide an improved drug delivery device for cartridges pre-filled with a liquid drug that eases the preparation of an injection while retaining the protection against accidental needle sticks as well as the protection of the liquid medicament from negative impacts during storage.

The aspects are implemented by a drug delivery device according to claim 1.

Exemplary embodiments of the disclosure are given in the dependent claims.

In the context of this specification, the terms distal and proximal are defined from the point of view of a person performing an injection. Consequently, a distal direction refers to a direction pointing towards the site of an injection and a distal end defines an end of an element that is directed towards the site of the injection. Respectively, the proximal end of an element or the proximal direction is directed away from the site of the injection and opposite to the distal end or distal direction.

According to the disclosure, a drug delivery device for dispensing a liquid drug comprises a body configured to house a cartridge comprising the liquid drug sealed with a septum and with a movable stopper, a needle holder holding a needle with a proximal and a distal needle tip relative to the body, and a cap adapted to cover at least the distal needle tip.

The cartridge is movable relative to the body from a retracted position towards an advanced position, wherein the proximal needle tip penetrates the septum when the cartridge holder is moved from its retracted into its advanced position. The cap is releasably engaged with the cartridge, wherein the cap is released from the cartridge in its advanced position.

While moving the cartridge towards the advanced position, the proximal needle tip pierces the septum and extends through the septum and the cap is being released from the cartridge. When the cartridge reaches its advanced position, the cap is released and, therefore, decoupled from the cartridge.

In order to prepare an injection, the cap is pulled off the drug delivery device in a distal direction. Alternatively, the drug delivery device is triggered so that the cartridge is advanced within the housing.

As the cap is engaged with the cartridge, the cartridge is moved from its retracted into its advanced position by pulling off the cap in the distal direction. Alternatively, after triggering of the drug delivery device, the cartridge is pushed forwards and takes along the cap.

Thereby, the proximal needle tip penetrates the septum such that the liquid drug can be expelled through the needle when the stopper of the cartridge is moved distally. Thus, the drug delivery device is prepared for an injection by pulling off the cap or by triggering the drug delivery device as a single user interaction. It is therefore not necessary to unpack and assemble a needle in such a drug delivery device with a cartridge. Thus, the same convenience and efficiency is reached as with prefilled syringes while advantageously retaining the liquid drug sealed in the cartridge for improved and prolonged storage.

In an embodiment of the drug delivery device, a cartridge holder holds the cartridge, wherein the cartridge holder comprises a lever protruding in a distal direction beyond the needle holder. On the distal end of the lever, a catch protrudes in an inwardly radial direction, i.e. directed towards a central longitudinal axis. The catch is releasably engaged with an angular recess formed in an inner surface of the needle cap, wherein the needle holder engages the lever such that the distal lever end is bended in an outwardly radial direction when the cartridge holder is moved towards the advanced position, thereby disengaging the radial catch from the angular recess. The needle holder may be formed as a socket with a radially protruding flange such that the lever engages and is bended by the flange.

As the catch via the lever reliably transfers a pulling force in a distal direction onto the cartridge holder, the cartridge holder is reliably brought towards its advanced position, thereby reliably penetrating the septum of the cartridge. As the catch disengages from the cap once the cartridge holder reached its advanced position, the cap can be removed from the drug delivery device particularly easy.

In another embodiment of a drug delivery device according to the disclosure, the cap has an at least partially folded collar on its open proximal end. The folded collar engages a shoulder of a wall of the cartridge in its retracted position. The at least partially folded collar is guided in a guide recess formed between the cartridge wall and the body when it is moved distally, thereby carrying the cartridge towards its advanced position. A proximal protrusion of the needle holder proximally protrudes the circular flange when the cartridge reaches its advanced position, thereby causing the folded collar to unfold and disengage from the circular flange. As the folded collar unfolds, the cap may easily be removed off the cartridge holder and off the drug delivery device.

In an embodiment, the folded collar may be formed by at least two circumference arms that engage the flange of the cartridge wall. The circumference arms may be formed as bended or folded splines that are unbent or unfolded when the cap is pulled distally such that corresponding proximal protrusions of the needle holder meet these folded splines, thereby disengaging the flange of the cartridge wall. The circumference arms may be led through openings in the body. Holding members of the body for holding the needle holder relative to the body are led through cut-outs in between the circumference arms.

In an embodiment of the drug delivery device, a stopper driver for driving the stopper in a distal direction is integrated into the cartridge holder. The stopper driver may be formed as a pre-stressed spring that, upon unblocking, effects between a proximal end of the cartridge holder and the stopper. As an advantage, upon unblocking or triggering the stopper driver, the liquid drug is expelled and thus injected automatically without further user interaction. As it is integrated into the cartridge holder, the distance that such a pre-stressed spring has to travel in order to reach the stopper is independent of the position of the cartridge holder, resulting in a continuous and steady ejection of the liquid drug.

In an embodiment of the drug delivery device, a stopper driver for driving the stopper in a distal direction is attached to the body. As multiple cartridges may be used with a single drug delivery device comprising a single stopper driver, such an embodiment may be more cost-effective and easier to manufacture and operate.

In an embodiment, the drug delivery device comprises a cartridge driver for driving the cartridge from the retracted towards the advanced position. As an advantage, the pulling force required to move the cartridge towards its advanced position may be reduced and an incomplete penetration of the septum by the proximal needle tip may be prevented.

In an embodiment, the cartridge driver comprises a pre-stressed spring which is particularly easy and cost-effective to manufacture.

In an embodiment, the cartridge driver is adapted to be released or triggered by pulling the cap, thereby relieving the user from the additional burden of releasing the cartridge driver. Those skilled in the art will acknowledge that other ways of releasing or triggering the cartridge driver are possible as well, such as pushing the sleeve or the body or a part thereof.

In an exemplary embodiment, the drug delivery device comprises a cartridge containing a drug.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given hereinbelow and the accompanying drawings which are given by way of illustration only, and thus, are not limitive of the present disclosure, and wherein:

FIGS. 4a-4d show a plurality of longitudinal sections of a drug delivery device with a cap with a partially folded collar in a sequence of steps during removal of the cap, and Corresponding parts are marked with the same reference symbols in all figures.

DETAILED DESCRIPTION

Figure 1:
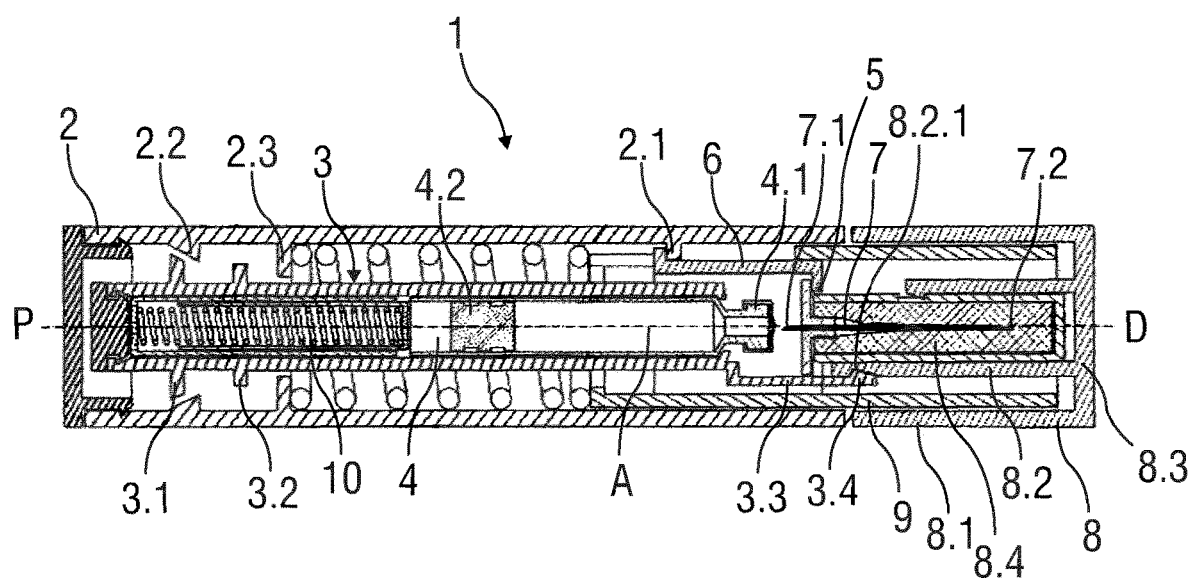
FIG. 1 is a longitudinal section of a drug delivery device with a cap with an angular recess and a cartridge holder in a retracted position.

FIG. 1 shows a drug delivery device 1 with a body 2 in a longitudinal section along a longitudinal axis A with a proximal end P and a distal end D. Inside the body 2, a cartridge holder 3 holds a cartridge 4 comprising a liquid drug.

The cartridge 4 is fixated relative to the cartridge holder 3. For example, the cartridge 4 may be pressed into the cartridge holder 3 such that it is held by friction. On its distal end, the cartridge 4 is sealed by a septum 4.1. On its proximal end, the cartridge 4 is sealed by a stopper 4.2 that is movable towards the distal end of the cartridge 4.

The cartridge holder 3 with the cartridge 4 is movable along the longitudinal axis A. On the proximal end of the cartridge holder 3, a clip 3.1 is arranged that protrudes in an outward radial direction, i.e. away from the central longitudinal axis A. An inclined flange of this outwardly radially protruding clip 3.1 engages an inwardly radially protruding wedge 2.2 with a correspondingly inclined edge. The inclination of the clip 3.1 and the corresponding inclination of the protruding wedge 2.2 are formed as to resist a distal displacement of the cartridge holder 3 such that an inadvertent movement of the cartridge holder 3 is prevented. When a sufficient force pulls the cartridge holder 3 in a distal direction, this resistance is overcome as the inclined flange of the clip 3.1 slides along the inclined edge of the protruding wedge 2.2, thereby slightly bending the body 2 outwardly. Once the clip 3.1 passed the wedge 2.2, the wedge 2.2 snaps beyond the proximal face of the clip 3.1 and blocks a proximal displacement of the cartridge holder 3.

An outwardly protruding stop 3.2 is formed on the cartridge holder 3 such that it engages a corresponding inwardly protruding flange 2.3 on the body 2 upon a predetermined distal displacement, thereby limiting the distal displacement range of the cartridge holder 3 with the cartridge 4.

Inside the body 2, a needle holder 5 is formed as a socket with a flange on its proximal end. The needle holder 5 is immovably attached to the body 2, for example by a pod 6 with radially protruding ends 6.1, 6.2, wherein the proximal radially protruding end 6.1 engages a proximal flange of a radial protrusion 2.1 of the body 2 and wherein the distal protruding end 6.2 engages the flange of the needle holder 5. Thereby the pod 6 prevents the needle holder 5 from withdrawing from the radial protrusion 2.1 in a distal direction. In its centre, the needle holder 5 holds a hypodermic needle 7. The needle 7 is immovable relative to the needle holder 5. For example, the needle 7 may be pressed into a central hole of the socket forming the needle holder 5 such that it is held by friction.

The needle 7 has a proximal needle tip 7.1 adapted to penetrate the septum 4.1 of the cartridge 4. In its retracted position shown in FIG. 1, the cartridge holder 3 with the cartridge 4 is proximally displaced such that the proximal needle tip 7.1 does not reach the septum 4.1, but the proximal needle tip 7.1 proximally protrudes the flange of the needle holder 5 such that the proximal needle tip 7.1 safely penetrates the septum 4.1 once the cartridge 4 is brought toward the needle holder 5. The needle 7 also has a distal needle tip 7.2 adapted to penetrate tissue on its distal end.

The distal part of the needle 7 is covered by a two-walled cap 8 that comprises an outer cap sheath 8.1, an inner cap sheath 8.2 concentrically arranged within the outer cap sheath 8.1 and a distal cap bottom 8.3. The inner cap sheath 8.2 holds a receptacle 8.4 that receives the distal part of the needle 7. The receptacle 8.4 may, for example, be made of rubber with a central hole closely fitting the distal part of the needle 7 such that the receptacle 8.4, and thereby the cap 8, are held by friction relative to the needle 7. By such a receptacle 8.4, the needle 7 is safely protected in a sterile environment. Those skilled in the art will appreciate that other embodiments of needle receptacles can be arranged inside the cap 8 as well.

The cartridge holder 3 comprises a bendable lever 3.3 protruding in a distal direction beyond the distal end of the cartridge 4 and further protruding beyond the flange of the needle holder 5. A radially protruding catch 3.4 is formed on the distal end of the lever 3.3 such that the tip of the catch 3.4 points towards the distal end D. The flange of the needle holder 5 engages the lever 3.3 such that it is slightly bended in an outward radial direction, i.e. away from the central longitudinal axis A.

An angular recess 8.2.1 is formed into the outer surface of the inner cap sheath 8.2 such that it receives the catch 3.4. Thereby, the catch 3.4 and the angular recess 8.2.1 form a snap-in closing between the cartridge holder 3 and the cap 8. While the cap 8 can easily be plugged onto the cartridge holder 3 during manufacturing, the snap-in closing formed by the catch 3.4 and the angular recess 8.2.1 locks the cap 8 and the cartridge holder 3 when the cap 8 is pulled off the drug delivery device 1 in preparation of an injection.

In the following, preparing the drug delivery device 1 for an injection is explained in more detail.

Figure 2:
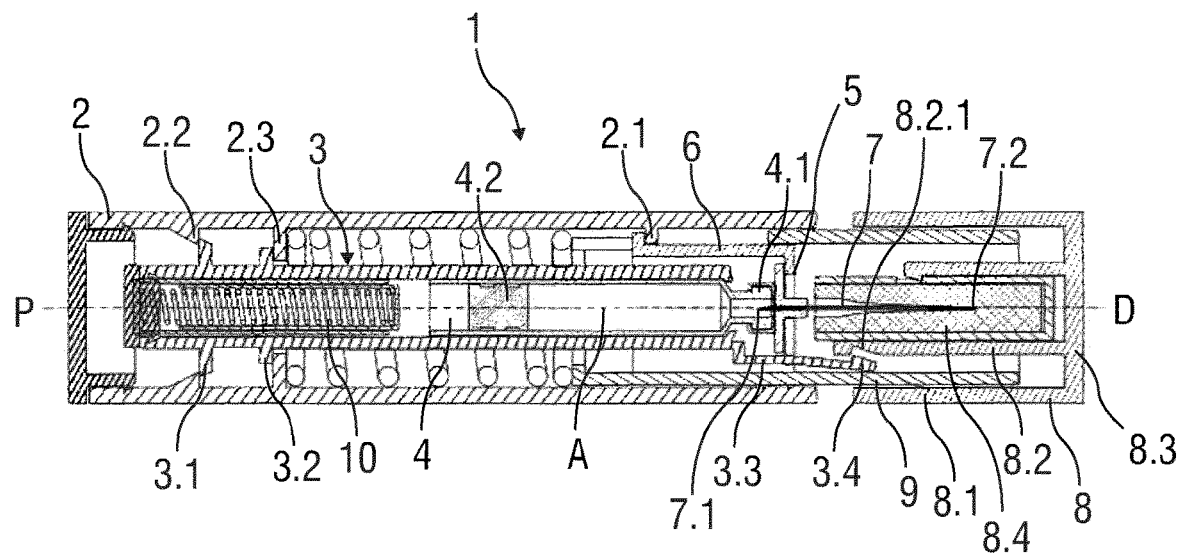
FIG. 2 is a longitudinal section of a drug delivery device with a cap with an angular recess and a cartridge holder in an advanced position.

When the cap 8 is pulled off the drug delivery device 1, the pulling force is transferred from the cap 8 via the catch 3.4 that is engaged in the angular recess 8.2.1 onto the cartridge holder 3. Thereby, the cartridge holder 3 is displaced distally into its advanced position that is shown in FIG. 2. In this advanced position, the cartridge 4 is brought towards the proximal surface of the needle holder 5 causing the proximal needle tip 7.1 to penetrate the septum 4.1. The cartridge holder 3 is locked in its advanced position by the stop 3.2 engaging the flange 2.3 and by the clip 3.1 engaging the wedge 2.2.

As the cartridge holder 3 moves from its retracted position in the distal direction, the lever 3.3 is bended outwardly by the needle holder 5. When the cartridge holder 3 reaches its advanced position, the lever 3.3 is just sufficiently bended to cause the catch 3.4 to disengage from the angular recess 8.2.1, thereby releasing the cap 8 from the cartridge holder 3.

Figure 3:
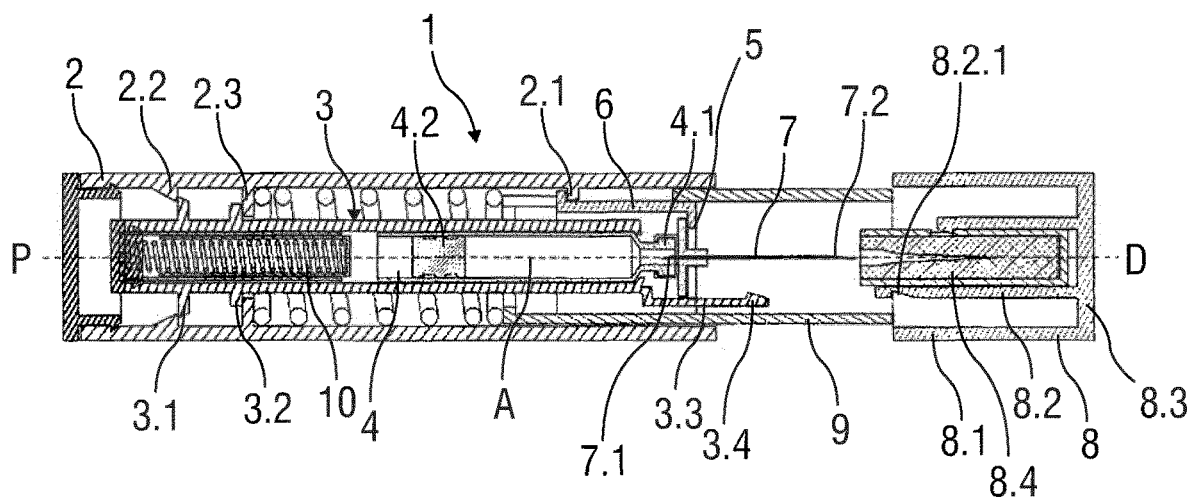
FIG. 3 is a longitudinal section of a drug delivery device with a cartridge holder in an advanced position after removal of a cap with an angular recess.

It is possible that the drug delivery device 1 comprises a slidable needle sleeve 9 that distally protrudes the body 2 to protect at least a distal part of the needle 7 to prevent needle stick injuries. In an embodiment, such a needle sleeve 9 is received in the space between the inner cap sheath 8.2 and the outer cap sheath 8.1. As it is shown in FIG. 3, in such an embodiment the cap 8 may be slid off the needle sleeve 9 once the catch 3.4 disengages from the angular recess 8.2.1. Pulling off the cap 8 is particularly easy, as the cartridge holder 3 is locked in its advanced position by the clip 3.1 and the stop 3.2, such that it cannot longer follow movements of the cap 8.

In an embodiment of the disclosure, the cartridge holder 3 further holds a stopper driver 10 for driving the stopper 4.2 in a distal direction in order to eject the liquid drug from the cartridge 4. The stopper driver 10 may be formed as a pre-compressed spring 10 integrated into the cartridge holder 3. Those skilled in the art will appreciate that other embodiments of a stopper driver are possible, such as a pre-compressed spring effecting between the stopper 4.2 and the body 2, for example a pre-compressed spring arranged between the stopper 4.2 and the proximal end of the body 2.

FIGS. 4A-4D show longitudinal sections of an embodiment of a drug delivery device 1 with a cap 18, depicting a sequence of steps for removing the cap 18 from the drug delivery device 1 and thereby preparing the drug delivery device 1 for an injection. According to this embodiment of the disclosure, the cartridge 4 has a cartridge wall 13. On the distal end of the cartridge the cartridge wall 13 has a shoulder 13.1 with a proximal flange. The cap 18 is formed as a sheath with an open proximal end, with a cap bottom 18.3 on its distal end and with a cap sleeve 18.1. The cap sleeve 18.1 provides at least one cut-out 18.1.2. On its proximal end, the cap sleeve 18.1 provides an at least partially folded collar 18.1.1.

Figure 4A:
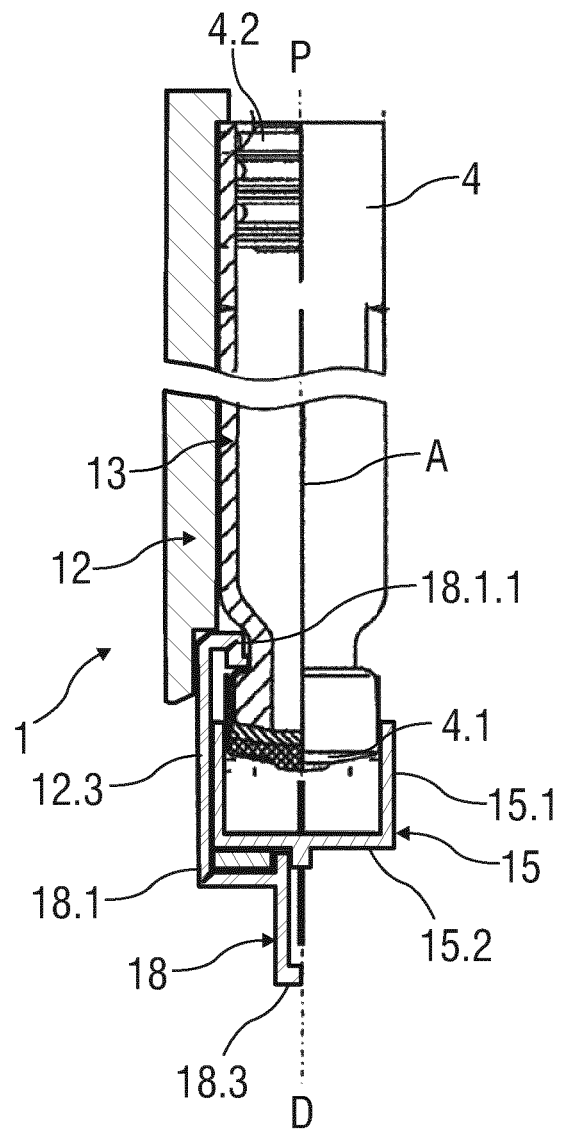

The at least partially folded collar 18.1.1 of the cap 18 engages the proximal flange of the shoulder 13.1 when the cartridge (4) is in its retracted position, as shown in FIG. 4A. A needle holder 15 is formed as a socket with a cylindrical side wall 15.1 and a bottom 15.2 on the distal end of the side wall 15.1, holding the needle 7 in a central hole of the bottom 15.2. The bottom 15.2, and thereby the needle holder 15, is fixated relative to the body 12 by at least one holding member 12.1 that is led through a cut-out 18.1.2 of the cap sleeve 18.1. The cap sleeve 18.1 is concentrically arranged to the side wall 15.1 of the needle holder 15. The proximal end of the cap sleeve 18.1 is led between the body 12 and the needle holder 15.

The cap sleeve 18.1 may be formed by at least two circumference arms, wherein the folded collar 18.1.1 on the proximal ends of these circumference arms is formed as bended or folded splines that engage the proximal flange of the shoulder 13.1. The circumference arms are led through openings 12.3 formed in the side wall of the body 12, such that holding members 12.1 are attached to the body 12 and led through cut-outs 18.1.2 in between the circumference arms forming the cap sleeve 18.1.

Figure 4B:
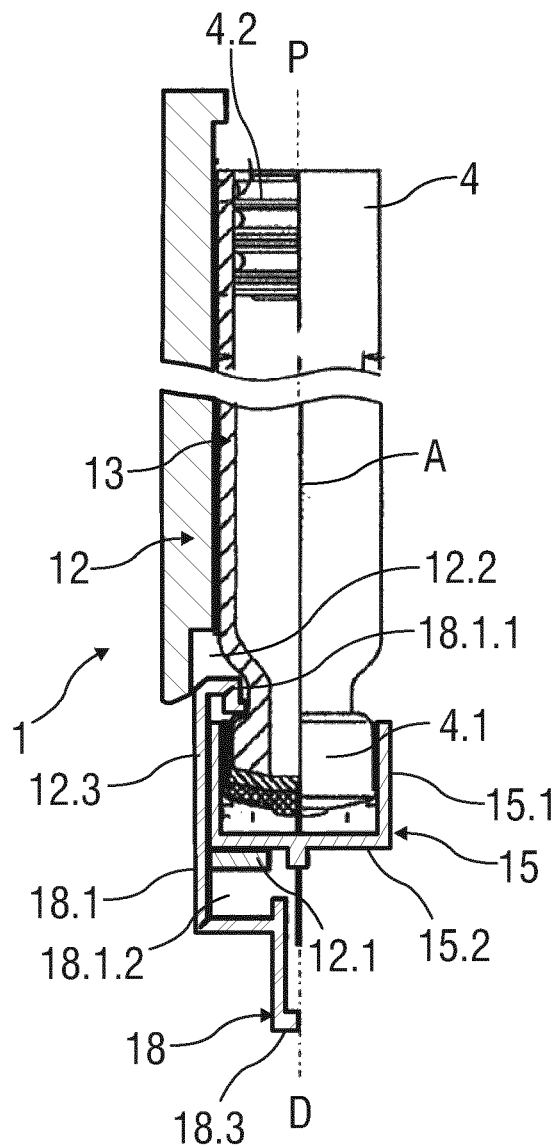

When the cap 18 is pulled off the drug delivery device 1, it carries the cartridge 4 in a distal direction, thereby causing the proximal needle tip 7.1 to penetrate the septum 4.1 of the cartridge 4, as shown in FIG. 4B. Unfolding of the folded collar 18.1.1 is prevented by guiding the cap sleeve 18.1 inside a recess 12.2 in the inner surface of the body 12. Those skilled in the art will appreciate that other embodiments of guiding the cap sleeve 18.1 inside the body 12 are possible.

The folded collar 18.1.1 may unbend or unfold through the opening 12.3 once the cartridge 4, carried by the cap 18, reached its advanced position, as shown in FIG. 4C. In this advanced position, the distal surface of the septum 4.1 engages the proximal surface of the bottom 15.2 of the needle holder 15, wherein the side wall 15.1 proximally protrudes the proximal flange of the shoulder 13.1. This proximal protrusion causes the folded collar 18.1.1 to unfold such that it disengages from the shoulder 13.1 and is released from the cartridge 4, as can be seen from FIG. 4D. The cap 18 can thus be easily removed from the drug delivery device 1 that is prepared for the injection.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 amino acid peptide which is produced by the salivary glands of the Gila monster), Liraglutide/ Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1 drug delivery device
2, 12 body
2.1 radial protrusion
2.2 wedge
2.3 flange
3 cartridge holder
3.1 clip
3.2 stop
3.3 lever
3.4 catch
4 cartridge
4.1 septum
4.2 stopper
5, 15 needle holder
6 pod
7 needle
7.1 proximal needle tip
7.2 distal needle tip
8, 18 cap
8.1 outer cap sheath
8.2 inner cap sheath
8.2.1 angular recess
8.3, 18.3 cap bottom
8.4 receptacle
9 needle sleeve
10 stopper driver
12.1 holding member
12.2 recess
12.3 opening
cartridge wall
13.1 shoulder
15.1 side wall
15.2 bottom
18.1 cap sleeve
18.1.1 folded collar
18.1.2 cut-out
19 trigger button
20 drive element
A longitudinal axis D distal end
P proximal end

The invention claimed is:

1. A drug delivery device for dispensing a liquid drug, the drug delivery device comprising:
- a body configured to house a cartridge comprising the liquid drug, the cartridge sealed with a septum and with a movable stopper;
- a needle holder holding a needle with a proximal needle tip and a distal needle tip relative to the body; and
- a cap adapted to cover at least the distal needle tip,
- wherein the cap is releasably engaged with the cartridge and the cartridge is movable relative to the body in a distal direction from a retracted position towards an advanced position, and
- wherein, while moving the cartridge towards the advanced position, the proximal needle tip pierces the septum, and the cartridge moves along with the cap in the distal direction, and
- wherein, when the cartridge reaches the advanced position, the cap is released from the cartridge.

2. The drug delivery device according to claim 1, wherein the cartridge is moved from the retracted position towards the advanced position when the cap is pulled off the drug delivery device in the distal direction and such that the cap is released from the cartridge in the advanced position.

3. The drug delivery device according to claim 1, wherein the cartridge is held by a cartridge holder comprising a lever protruding in the distal direction beyond the needle holder with a catch protruding on a distal lever end in an inwardly radial direction that is releasably engaged with an angular recess formed in an inner surface of the needle cap, wherein the needle holder engages the lever such that the distal lever end is bended in an outwardly radial direction when the cartridge holder is moved towards the advanced position, thereby disengaging the catch from the angular recess.

4. The drug delivery device according to claim 1, wherein an at least partially folded collar on a proximal end of a cap sleeve of the cap releasably engages a shoulder of a cartridge wall of the cartridge and is guided in a guide recess formed between the cartridge wall and the body, and wherein a side wall of the needle holder proximally protrudes the shoulder when the cartridge wall reaches its advanced position, thereby causing the at least partially folded collar to unfold and disengage from the shoulder.

5. The drug delivery device according to claim 4, wherein the cap sleeve is formed by at least two circumference arms, each led through a side opening in the body, and wherein the at least partially folded collar is formed by bended or folded splines on the proximal ends of the at least two circumference arms.

6. The drug delivery device according to claim 1, wherein a stopper driver for driving the stopper in the distal direction is integrated into the cartridge holder.

7. The drug delivery device according to claim 1, wherein a stopper driver for driving the stopper in the distal direction is attached to the body.

8. The drug delivery device according to claim 1, further comprising a cartridge driver for driving the cartridge from the retracted position towards the advanced position.

9. The drug delivery device according to claim 8, wherein the cartridge driver comprises a pre-stressed spring.

10. The drug delivery device according to claim 8, wherein the cartridge driver is adapted to be released by pulling the cap.

11. The drug delivery device according to claim 1, wherein the cartridge contains a drug.

* * * * *

UNITED STATES PATENT AND TRADEMARK OFFICE
CERTIFICATE OF CORRECTION

PATENT NO. : 10,675,411 B2  
APPLICATION NO. : 15/736617  
DATED : June 9, 2020  
INVENTOR(S) : Marc Schader et al.

Page 1 of 1

It is certified that error appears in the above-identified patent and that said Letters Patent is hereby corrected as shown below:

On the Title Page

On page 2, item (57) Column 1 (Abstract), Line 4, delete "tipthrough" and insert -- tip through --

In the Specification

In Column 1, Line 12 (approx.), delete "in on" and insert -- on --

Signed and Sealed this  
Twentieth Day of October, 2020

Andrei Iancu  
*Director of the United States Patent and Trademark Office*